US00PP34867P2

(12) United States Plant Patent
Clark

(10) Patent No.: US PP34,867 P2
(45) Date of Patent: Dec. 27, 2022

(54) BLACKBERRY PLANT NAMED 'APF-268'

(50) Latin Name: ***Rubus* subgenus *Rubus* Watson**
Varietal Denomination: APF-268

(71) Applicant: THE BOARD OF TRUSTEES OF THE UNIVERSITY OF ARKANSAS, Little Rock, AR (US)

(72) Inventor: John R. Clark, Fayetteville, AR (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 0 days.

(21) Appl. No.: 17/532,275

(22) Filed: Nov. 22, 2021

(51) Int. Cl.
*A01H 6/74* (2018.01)
*A01H 5/08* (2018.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP8,510 | P | 12/1993 | Moore |
| PP11,861 | P2 | 5/2001 | Clark |
| PP11,865 | P2 | 5/2001 | Clark |
| PP14,935 | P2 | 6/2004 | Clark |
| PP15,788 | P2 | 6/2005 | Clark |
| PP16,989 | P3 | 8/2006 | Clark |
| PP17,162 | P3 | 10/2006 | Clark |
| PP17,983 | P2 | 9/2007 | Cabrera Avalos |
| PP20,891 | P3 | 3/2010 | Clark |
| PP22,449 | P3 | 1/2012 | Clark |
| PP23,497 | P3 | 3/2013 | Clark |
| PP24,249 | P3 | 2/2014 | Clark |
| PP25,864 | P3 | 9/2015 | Clark |
| PP26,120 | P3 | 11/2015 | Clark |
| PP26,368 | P3 | 2/2016 | Banados Ortiz |
| PP26,405 | P3 | 2/2016 | Clark |
| PP26,413 | P3 | 2/2016 | Ortiz |
| PP26,990 | P3 | 8/2016 | Clark |
| PP27,032 | P2 | 8/2016 | Clark |
| PP27,401 | P3 | 11/2016 | Clark |
| PP28,598 | P3 | 11/2017 | Clark |

OTHER PUBLICATIONS

Segantini et al. Physiochemical Changes in Floricane and Primocane Blackberries Harvested from Primocane Genotypes. HortScience vol. 53 (2018) Issue 1 (Jan. 2018).*
Clark, J.R. et al., "'APF-45' primocane-fruiting blackberry," (2011) Hort. Science 46(4):670-673.
Ruple, A. et al., "An evaluation of fertility in Arkansas primocane-fruiting blackberries," (2010) Hort. Science 45:1-6.
Daugovish, O., et al. "Blackberry and Raspberry Cultivar Evaluations in Coastal California." HortTechnology 31.4 (2021): 552-558.

* cited by examiner

*Primary Examiner* — Annette H Para
(74) *Attorney, Agent, or Firm* — Quarles & Brady LLP

(57) ABSTRACT

Description and specifications of a new and distinct cultivar of blackberry plant named 'APF-268' which originated from seed produced by a hand-pollinated cross of Arkansas selections 'APF-45' (U.S. Plant Pat. No. 22,449) x 'APF-158' (non-patented, unreleased genotype) is provided. This new cultivar of blackberry plant can be distinguished by its large fruit with consistent size and sweet flavor. The plants have consistently good plant health and primocane-fruiting habit.

4 Drawing Sheets

Latin name: *Rubus* subgenus *Rubus* Watson.
Varietal denomination: 'APF-268'.

BACKGROUND

The new primocane-fruiting blackberry plant called 'APF-268' is described herein. The new plant originated from a hand-pollinated cross of Arkansas selections 'APF-45' (U.S. Plant Pat. No. 22,449) x 'APF-158' (non-patented, unreleased genotype) made in 2008. The seeds resulting from this controlled hybridization were germinated in a greenhouse in the spring of 2009 and planted in a field near Clarksville, Ark. (West-Central Arkansas). The seedlings fruited in the summer of 2010 and one seedling, designated 'APF-268' was selected. It was selected for its mid to late fruiting season, consistently large fruit with balanced flavor, good plant health, and heavy primocane-fruiting potential.

SUMMARY OF THE INVENTION

The new and distinct cultivar of blackberry originated from a hand-pollinated cross of Arkansas selections 'APF-45' (U.S. Plant Pat. No. 22,449) x 'APF-158' (not patented, unreleased genotype) made in 2008 and located near Clarksville, Ark. (West-Central Arkansas). The botanical designation of the new cultivar of blackberry is *Rubus* L. subgenus *Rubus* Watson. The seeds resulting from this controlled hybridization were germinated in a greenhouse in the winter to early spring of 2009 and planted in a field near Clarksville, Ark. The seedlings fruited in the summer of 2010 on floricanes and one seedling, designated 'APF-268', was selected for its mid to late fruiting season, consistently large fruit with balanced flavor, good plant health, and primocane-fruiting habit.

During winter 2010-11, the original plant selection was propagated asexually from root cuttings at the above-noted location, and a test row of 10 plants were established.

The new cultivar has been asexually multiplied since 2010 by the use of root cuttings in Clarksville, Ark., by rooting adventitious shoots from root cuttings and tissue culture. It forms new shoots from adventitious buds on root cuttings readily. During all asexual multiplication, the characteristics of the original plant have been maintained and no aberrant phenotypes have appeared.

The cultivar differs from most blackberry cultivars which are floricane fruiting.

BRIEF DESCRIPTION OF THE PHOTOGRAPHS

The accompanying photographs show typical specimens of the new variety in color as nearly true as it is reasonably possible to make in a color illustration of this character. The plants shown in the figures are three years of age.

DETAILED DESCRIPTION OF THE NEW CULTIVAR 'APF-268'

Figure 1:
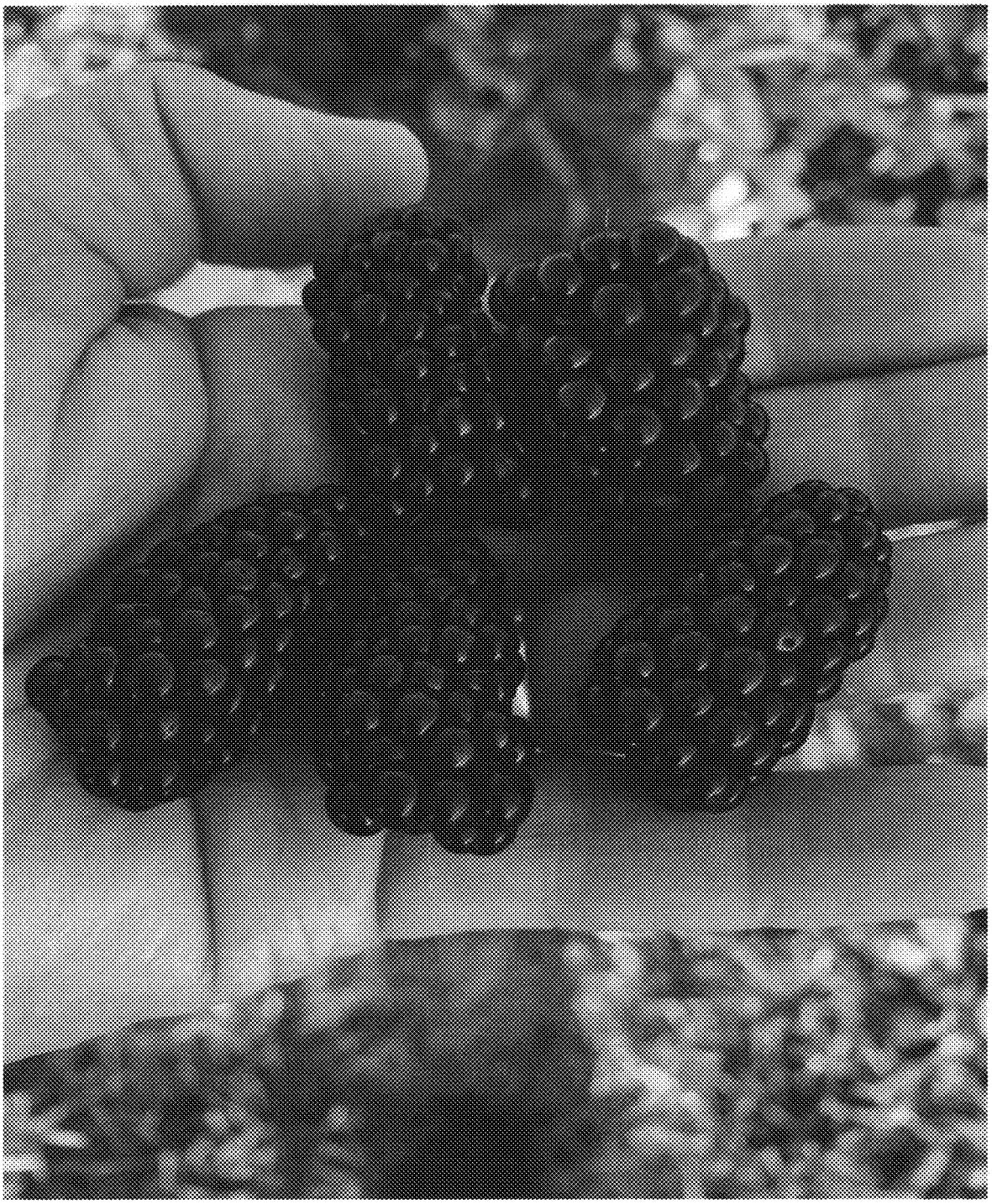
FIG. 1 is a photograph of fruits of 'APF-268' borne on a floricane in mid-June, near Clarksville, Ark.
Figure 2:
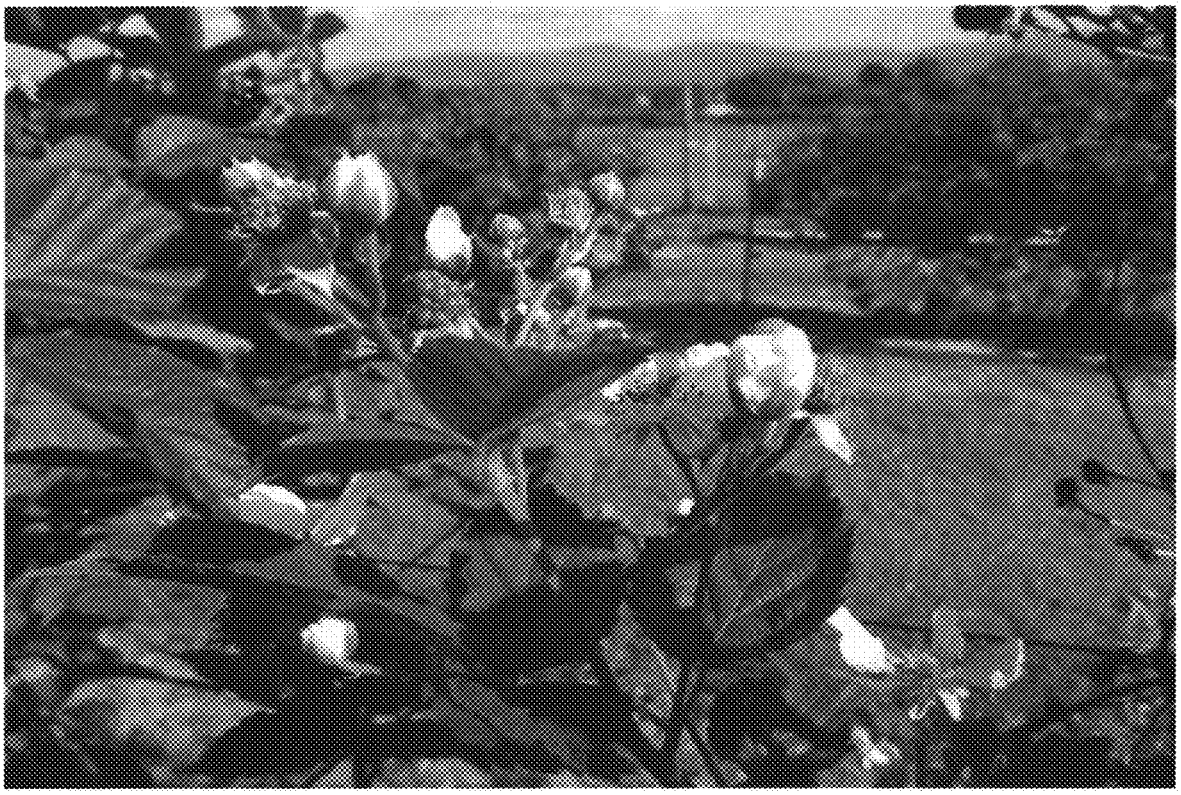
FIG. 2 is a photograph of primocane flowers and flower buds, near Clarksville, Ark. of 'APF-268'.
Figure 3:
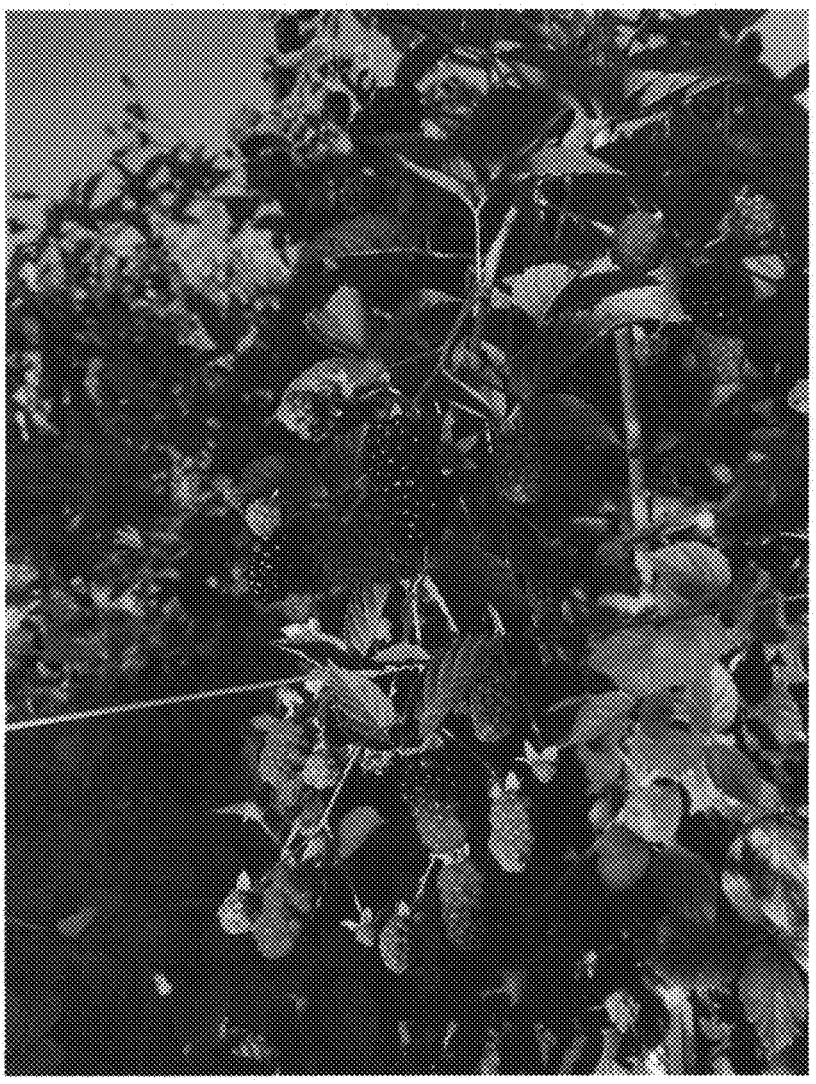
FIG. 3 is a photograph of primocane fruit of 'APF-268', near Clarksville, Ark.
Figure 4:
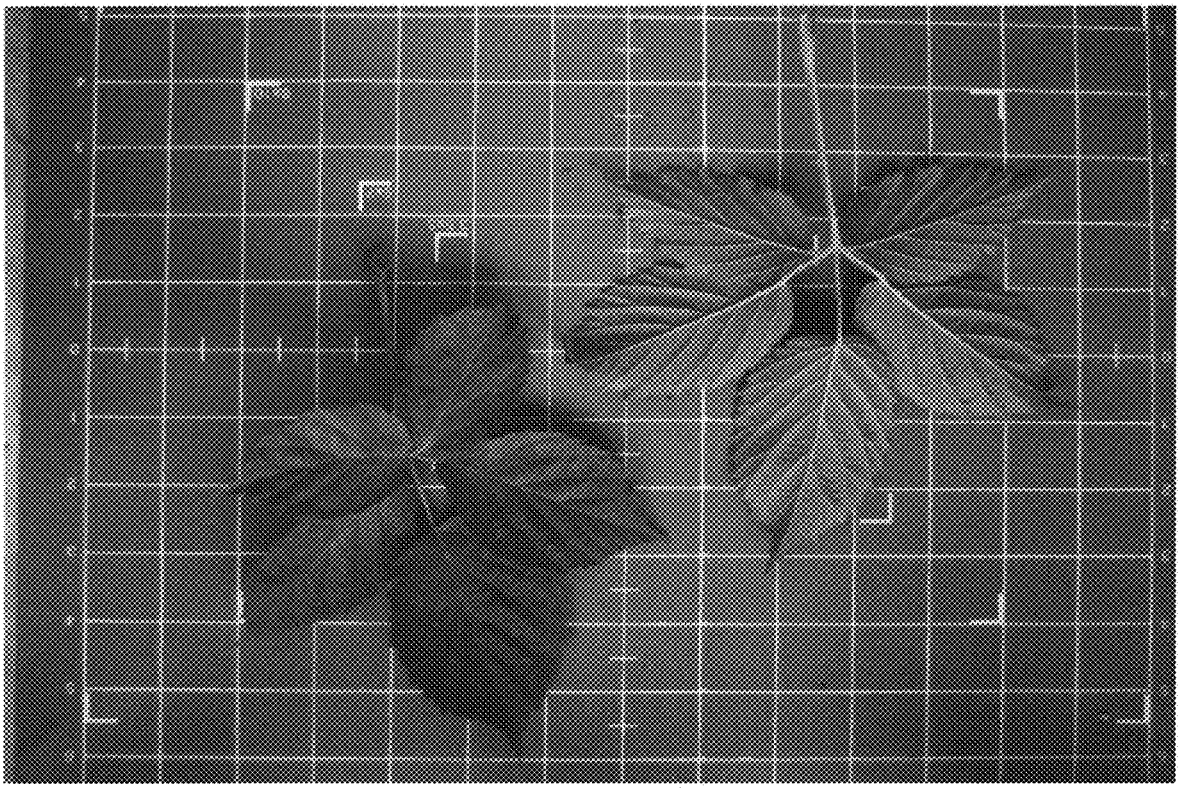
FIG. 4 is a photograph showing the abaxial (right) and adaxial (left) surfaces of primocane leaves, near Clarksville, Ark. of 'APF-268'.

Plants and fruit of this new cultivar differ phenotypically from its parents. The new blackberry plant has a later floricane-fruiting season and longer harvest period compared to its female parent 'APF-45'. The new cultivar ripens later and has larger fruit than its male parent 'APF-158.' Although blackberries (*Rubus* L. subgenus *Rubus* Watson) are highly heterogeneous and outcrossing, and most clones contain genes from more than one species, the new cultivar and its progenitor lines phenotypically exhibit characters predominately of the erect eastern United States species, *Rubus allegheniensis* Porter (highbush blackberry).

Plants of the new cultivar are vigorous and prolific and row establishment following planting is rapid. Both primocanes and floricanes are erect in growth habit. The canes are best managed if trained to a hedgerow and a trellis with supporting wires used to prevent canes from falling over due to wind or heavy fruit loads. The plants are thorny. Plants and fruit are moderately resistant to anthracnose [*Elsinoe veneta* (Burkh.) Jenkins], and plants have shown no evidence of susceptibility to orange rust [*Gymnoconia nitens* (Schwein.) F. Kern and H. W. Thurston.]. No screening has been done for resistance to double blossom/rosette [*Cercosporella rubi* (Wint.) Plakidas].

The floricane bloom period of the new cultivar begins on 19 April, compared to 16 April for 'APF-45'. Primocane bloom period begins 25 June compared to 29 June for 'APF-45'. Floricane fruit of the new cultivar has a harvest period of 40 days. Primocane first ripe fruit date is 10 August on tipped primocanes, whereas 'APF-45' is 13 August. Primocane fruit harvest can be dependent on environmental conditions, most importantly temperatures being below 32° C. (90° F.) to allow fruiting. In Clarksville, Ark., the primocane-fruit harvest period is over 60 days.

Fruit yields of the new cultivar on floricanes are usually 4.3 kg/plant (9.5 lb/plant) if the floricanes are retained for fruiting, compared to 3.8 kg/plant (8.3 lb) for 'APF-45' in West-Central Arkansas. Fruit yields of the new cultivar on primocanes in West-Central Arkansas average 1.2 kg/plant (2.6 lb/plant compared to 1.4 kg (3.1 lb/plant) for 'APF-45'.

The fruit shape is oblong, bright glossy black in color, and very attractive. The floricane fruit is large (7.8 g), slightly larger than 'APF-45', which averaged 6.9 g. Primocane fruit in West-Central Arkansas of the new cultivar averaged 7.2 g/berry, 2.1 g larger than primocane fruit of 'APF-45' (ave. 5.3 g). The berries have a firm texture and good postharvest storage potential, comparable to 'APF-45'. The dry seed weight of floricane fruit for the new cultivar averaged 3.4 mg/seed, smaller than for 'APF-45' (4.5 mg), 'Natchez' (U.S. Plant Pat. No. 20,891) (4.2 mg), and 'Ouachita' (U.S. Plant Pat. No. 17,162) (4.5 mg).

The fresh fruit rates good in flavor, comparable to comparison cultivars. The soluble solids concentration averages 9.6% on shiny black fruit harvested from floricanes and is the similar for primocane fruit (9.5%). Soluble solid content is lower than that of 'APF-45' which averages 10.9% for floricane fruit and 11.4% for primocane fruit.

Primocane fruit and flowers are borne on the cane terminus or on lateral branches if primocanes are tipped, and fruiting continues down the primocane during the season. Canes usually attain a length of 1.5 to 1.8 m (4-5 ft) prior to the appearance of flower buds. The number of nodes down the cane that develop flowers is largely dependent on the length and conditions of the late summer to fall growing period.

The following is a detailed description of the botanical and pomological characteristics of the subject blackberry. Color data are presented in Royal Horticultural Society Colour Chart designations (1986 2nd edition). Where dimensions, sizes, colors, and other characteristics are given, it is to be understood that such characteristics are approximations of averages set forth as accurately as practicable.

Plants used for botanical data were three years old and grown on a fine sandy loam soil with trickle irrigation near Clarksville, Ark. The plants were fertilized near budbreak (February to March) with complete or nitrogen fertilizer, and had an additional nitrogen fertilizer application in early July. Primocanes were tipped at approximately 1.14 m (45 inches), and grown in a hedgerow training system. Weeds were controlled with pre- and post-emergence herbicides supplemented with mechanical weed control activities. A single application of liquid lime sulfur was applied to the plants at budbreak, but no other fungicides were used. The descriptions reported herein are from specimens grown near Clarksville, Ark.

Plant:

*Size*.—Medium. Plants are grown in a hedgerow and primocanes tipped at approx. 114 cm; plants in this system range in size from approx. 135-140 cm tall and 91-102 cm wide.

*Growth habit*.—Moderate vigor, canes erect; suckers primarily from the crown of the plant.

*Growth rate*.—First emergence of primocanes is 12 April and primocanes reach tipping height (114 cm) approximately 18 May.

Productivity:

*Floricane*.—4.3 kg/plant (9.5 lb/plant).

*Primocane*.—1.2 kg/plant (2.6 lb/plant).

*Cold hardiness*.—Hardy to −17° C. (1° F.) and possibly lower.

*Canes*.—Thorny, erect.

*Disease resistance*.—Moderate resistance to anthracnose, and no evidence of orange rust disease. No screening has been done for resistance to double blossom/rosette.

Floricane (dormant or winter cane):

*Cane diameter*.—Base: 1.43 cm; midpoint: 1.12 cm; terminus: 0.87 cm.

*Internode length*.—Base: 9.92 cm; midpoint: 8.45 cm; terminus: 5.06 cm.

*Floricane color*.—Base: greyed-purple group 185A on sun exposed side, yellow-green group 144B on shaded side; midpoint: greyed-purple group 187B on sun exposed side, yellow-green group 144B on shaded side; terminus: greyed-purpled group 184A on sun exposed side, yellow-green group 144B on shaded side.

*Thorn density/30 cm*.—Base: 3; midpoint: 7; terminus: 8.

*Thorn size*.—Base width: 3.30 mm; midpoint width: 0.79 mm; apex width: 0.30 mm; thorn height: 5.11 mm.

*Thorn color*.—Greyed-purple group 185B.

*Lateral branching after tipping* (*measured at the end of growing season*).—Average number of lateral branches: 6; distribution: distal, top one-third of canes; anthocyanin present: yes; color: greyed-purple group 185A.

*Shape of dormant cane cross-section*.—Angular to round.

Primocane (current-season cane):

*Date of primocane emergence*.—12 April.

*Number of new canes per season*.—6.

*Cane diameter*.—Base: 1.37 cm; midpoint: 1.28 cm; terminus: 0.58 cm.

*Internode length*.—Base: 8.70 cm; midpoint: 7.56 cm; terminus: 2.90 cm.

*Primocane color*.—Base: yellow-green group 146B; midpoint: yellow-green group 146B; terminus: yellow-green group 144A. No anthocyanin coloration present on primocanes.

*Thorn density/30 cm*.—Base: 2; midpoint: 8; terminus: 15.

*Thorn size*.—Base width: 3.41 mm; midpoint width: 0.95 mm; apex width: 0.29 mm; thorn height: 5.28 mm.

*Thorn color*.—Yellow-green group 144A.

*Lateral branching after tipping* (*measured at the end of growing season*).—Average number of lateral branches: 2; distribution: distal, top one-third of canes.

*Relative number of glandular hairs on young shoot*.—Present, low concentration of glandular hairs.

Foliage (floricane):

*Leaves*.—Shape: compound palmate leaf; size: Medium; mature compound leaf; width 11.72 cm; length 8.31 cm; budbreak: 10 February.

*Glossiness*.—Abaxial: dull, not glossy; adaxial: faint glossiness.

*Leaflet*.—Width: 4.26 cm; length: 6.98 cm; shape: ovate with acute apex and rounded base; margin: biserrate; serration teeth length: 3.86 mm; width: at base: 2.91 mm; shape in cross section: v-shaped; degree of undulation on terminal leaflet: none; degree of blistering on terminal leaflet: none.

*Pubescence*.—Abaxial: lightly present; adaxial: absent.

*Number of leaflets per compound leaf*.—3.

*Leaf color*.—Base: abaxial: yellow-green group 147B, adaxial: green group 139A; midpoint: abaxial: yellow-green group 147B, adaxial: green group 139A; terminus: abaxial: abaxial: yellow-green group 147B, adaxial: green group 139A.

*Petioles*.—Length: 2.99 cm; diameter: 1.47 mm color: yellow-green group 146B; texture: moderate pubescence.

*Petiolules*.—Length: 1.25 cm; diameter: 0.99 mm color: yellow-green group 146B; texture: smooth, light pubescence.

*Stipule*.—Number present: 2.

*Stipule size*.—Length: 0.75 cm; width: 0.20 cm.

*Stipule shape*.—Overall: lanceolate; apex: acute; margin: entire (smooth); base: acuminate.

*Stipule texture*.—Abaxial: light pubescence; adaxial: light pubescence.

*Stipule color*.—Abaxial: Yellow-green group 144B; adaxial: yellow-green group 144A.

*Venation pattern*.—Pinnate.

*Vein color* (*mature leaves*).—Abaxial: yellow-green group 146C; adaxial: yellow-green group 146A.

*Vein color* (*young leaves*).—Abaxial: yellow-green group 148A; adaxial: yellow-green group 147C.

Foliage (primocane):

*Leaves*.—Shape: compound palmate leaf; size: Medium; mature compound leaf: width: 16.19 cm; length 15.63 cm.

*Glossiness*.—Abaxial: dull, not glossy; adaxial: faint glossiness.

*Leaflet*.—Width: 6.62 cm; length: 9.25 cm; shape: ovate with acute apex and rounded base; margin: biserrate; serration teeth length: 2.73 mm; width: at base: 3.01 mm; shape in cross section: v-shaped; degree of undulation on terminal leaflet: none; degree of blistering on terminal leaflet: none.

*Pubescence*.—Abaxial: lightly present; adaxial: absent.

*Number of leaflets per compound leaf*.—5.

*Leaf color*.—Base: abaxial: yellow-green group 147B, adaxial: green group 139A; midpoint: abaxial: yellow-green group 147B, adaxial: green group 139A; terminus: abaxial: abaxial: yellow-green group 147B, adaxial: green group 139A.

*Petioles*.—Length: 6.35 cm; diameter: 1.47 mm color: yellow-green group 144A; texture: light pubescence.

*Petiolules*.—Length: 2.70 cm; diameter: 0.96 mm color: yellow-green group 146B; texture: smooth with light pubescence.

*Stipule*.—Number present: 2.

*Stipule size*.—Length: 9.81 mm; width: 0.67 mm.

*Stipule shape*.—Overall: lanceolate; apex: acute; margin: entire (smooth); base: acuminate.

*Stipule texture*.—Abaxial: light pubescence; adaxial: light pubescence.

*Stipule color*.—Abaxial: Yellow-green group 144A; adaxial: yellow-green group 144A.

*Venation pattern*.—Pinnate.

*Vein color* (*mature leaves*).—Abaxial: green group 143C; adaxial: yellow-green group 145A.

*Vein color* (*young leaves*).—Abaxial: green group 143C; adaxial: yellow-green group 145A.

Flowers (floricane):

*Date of first bloom.*—19 April.

*Petal color.*—Abaxial: white group 155C; adaxial: white group 155C.

Reproductive organs:

*Stamens.*—Numerous.

*Pistils.*—Numerous.

*Pollen.*—Normal, fertile, and abundant.

*Flower.*—Size: Diameter: 5.15 cm; depth: 1.91 cm; shape: overall: rotate; symmetry: actinomorphic.

*Petal size.*—Length 2.63 cm; width 1.81 cm.

*Petal shape.*—Overall: obovate; apex: obtuse; margin: smooth (entire); base: acuminate.

*Petal texture.*—Abaxial: no pubescence; adaxial; no pubescence.

*Average number flowers per cluster.*—6.

*Average number of petals per flower.*—6.

*Sepals.*—Length 0.94 cm; width: 0.46 cm; shape: overall: lanceolate; apex: acute; margin: smooth (entire); base: truncate; texture: abaxial: moderate-heavy pubescence; adaxial: heavy pubescence; color: abaxial: yellow-green group 144A; adaxial: yellow-green group 146D; number per flower: 5.

*Pedicel.*—Length: 5.88 cm; diameter: 1.39 mm; color: green group 143B; texture: moderate pubescence present.

*Peduncle.*—Size: length: 3.70 cm; width: 2.65 mm; color: green group 143C.

*Cyme type.*—Simple cyme; length: 45.69 cm.

Flowers (primocane):

*Date of bloom.*—First bloom 25 June and can extend until frost depending on environment and cultural management.

*Petal color.*—Abaxial: white group 155D; adaxial: white group (155D).

Reproductive organs:

*Stamens.*—Numerous.

*Pistils.*—Numerous.

*Pollen.*—Fertile and abundant unless temperatures exceed 32° C. (90° F.) at which temperature can damage flowers and anthers and pollen production can be reduced.

*Flower.*—Size: diameter: 3.17 cm; depth: 1.70 cm; shape: overall: rotate; symmetry: actinomorphic.

*Petal size.*—Length: 1.98 cm; width: 1.13 cm.

*Petal shape.*—Overall: obovate; apex: obtuse; margin: smooth (entire); base: acuminate.

*Petal texture.*—Abaxial: no pubescence; adaxial: no pubescence.

*Average number flowers per cluster.*—12.

*Average number of petals per flower.*—6.

*Sepals.*—Length 0.70 cm; width: 0.46 cm; shape: overall: lanceolate; apex: acute; margin: smooth (entire); base: truncate; texture: abaxial: moderate pubescence; adaxial: heavy pubescence; color: abaxial: yellow-green group 144A; adaxial: yellow-green group 146D; number per flower: 5.

*Pedicel.*—Length: 3.41 cm; diameter: 1.31 mm; color: yellow-green group (144A); texture: moderate pubescence.

*Peduncle.*—Size: length: 2.14 cm; width: 1.21 mm; color: green group 143A.

*Cyme type.*—Elongated simple cyme; length: 23.65 cm.

Fruit (floricane):

*Maturity.*—Average first ripe date 14 June.

*Size.*—Large, average 7.8 g.

*Diameter of fruit at primary position on inflorescence.*—Equator: 2.05 cm; base pole: 1.78 cm; terminus pole: 1.09 cm.

*Diameter of fruit at secondary positions on inflorescence.*—Equator: 1.83 cm; base pole: 1.74 cm; terminus pole: 1.32 cm.

*Length (primary fruit).*—3.46 cm.

*Length (secondary fruit).*—2.99 cm.

*Length (tertiary fruit).*—2.94 cm.

*Shape.*—Oblong.

*Color.*—Black group 202A.

*Drupelet size.*—0.51 cm.

*Drupelets per berry.*—87.

*Seed size.*—Length: 3.44 mm; width: 2.74 mm.

*Seed weight.*—Wet: 3.86 mg; dry 3.40 mg.

*Seed color.*—Wet: greyed-red group 178C; dry: greyed-orange group 166B.

*Soluble solids.*—9.6%.

*pH.*—3.08.

*Titratable acidity.*—0.99% citric acid.

*Processed quality.*—Not evaluated for processing.

*Uses.*—For home garden, local fresh-market, or commercial shipping.

Fruit (primocane):

*Maturity.*—Average first ripe date 10 August on tipped primocanes and can fruit until frost depending on environment and cultural management.

*Size.*—Large, 7.2 g/berry.

*Diameter of fruit at primary position on inflorescence.*—Equator: 2.29 cm; base pole: 2.26 cm; terminus pole: 1.48 cm.

*Diameter of fruit at secondary positions on inflorescence.*—Equator: 2.26 cm; base pole: 2.07 cm; terminus pole: 170 cm.

*Length (primary fruit).*—2.82 cm.

*Length (secondary fruit).*—2.10 cm.

*Length (tertiary fruit).*—2.51 cm.

*Shape.*—Oblong.

*Color.*—Black group 202A.

*Drupelet size.*—0.68 cm.

*Drupelets per berry.*—50.

*Seed size.*—Length: 4.31 mm; width: 2.83 mm.

*Seed weight.*—Wet: 4.26 mg; dry 3.38 mg.

*Seed color.*—Wet: red-purple group 59B; dry: greyed-orange group 165C.

*Soluble solids.*—9.9%.

*pH.*—2.92.

*Titratable acidity.*—0.79% citric acid.

*Processed quality.*—Not evaluated for processing.

*Uses.*—For home garden, local fresh-market, or commercial shipping.

The cultivar: The most distinctive features of the new cultivar of blackberry plant are mid to late fruiting season, consistently large fruit with balanced flavor, good plant health, and heavy primocane-fruiting potential.

I claim:

1. A new and distinct cultivar of blackberry plant named 'APF-268', substantially as illustrated and described.

* * * * *